United States Patent [19]

Michaelis

[11] 4,088,798

[45] May 9, 1978

[54] METHODS FOR THE PREPARATION OF CONTROLLED GASTRIC RESIDENCE TIME MEDICAMENT FORMULATIONS

[75] Inventor: Arthur F. Michaelis, Basking Ridge, N.J.

[73] Assignee: Sandoz, Inc., E. Hanover, N.J.

[21] Appl. No.: 744,255

[22] Filed: Nov. 23, 1976

Related U.S. Application Data

[63] Continuation of Ser. No. 630,901, Nov. 11, 1975, abandoned.

[51] Int. Cl.² .............................................. A61K 9/00
[52] U.S. Cl. ......................................... 427/3; 424/33; 424/19
[58] Field of Search ................ 526/49; 427/3; 424/33, 424/19

[56] References Cited

U.S. PATENT DOCUMENTS

| 3,143,472 | 8/1964 | Lappas ..................................... 424/33 |
| 3,407,157 | 10/1968 | Carstensen ............................... 424/33 |
| 3,442,698 | 5/1969 | Dill ..................................... 526/49 X |
| 3,878,151 | 3/1975 | Dach .................................. 526/49 X |
| 3,959,540 | 5/1976 | Leiberich ............................. 427/3 X |

*Primary Examiner*—Ronald H. Smith
*Assistant Examiner*—Sam Silverberg
*Attorney, Agent, or Firm*—Gerald D. Sharkin; Robert S. Honor; Walter F. Jewell

[57] ABSTRACT

Controlled gastric residence time medicament formulations, e.g., tablets and/or capsules, containing polymeric film coatings are exposed to a volatile amine, e.g., anhydrous ammonia, methyl amine, or ethyl amine, to provide improved medicament formulations, which by virtue of mechanical or surface effects including expansion or swelling of the coating in gastric fluids are capable of prolonged, e.g., up to twelve hours, residence in the gastric area.

8 Claims, No Drawings

METHODS FOR THE PREPARATION OF CONTROLLED GASTRIC RESIDENCE TIME MEDICAMENT FORMULATIONS

This is a continuation of application Ser. No. 630,901 filed Nov. 11, 1975 now abandoned.

This invention relates to medicament formulations. More particularly, it relates to a method of preparing controlled gastric residence time medicament formulations and to the sustained or controlled release of drugs from the formulations into body fluids.

Nearly all drugs are best absorbed in one particular region of the gastrointestinal tract; either in the gastric region and upper small intestine or in the middle or further region of the small intestine. Following oral administration, acidic drug moieties, based on their ionization properties, are best absorbed in the upper gastrointestinal tract, i.e., stomach or upper small intestine. Basic drug moieties on the other hand will be best absorbed outside the gastric region and at a point in the small intestine where the pH has reached a value of three or above.

Even basic and amphoteric drug moieties which are absorbed outside the gastric region may have improved availability if the residence time in the gastric area is prolonged. Most basic and many amphoteric drug moieties are soluble in the gastric region where they form an acid salt. Further along the gastrointestinal tract in their undissociated form they become absorbed. Some basic and amphoteric drug compounds, however, which do not dissolve in the stomach because of premature emptying, and/or a low order of solubility, or a slow solubility rate, will also not dissolve in the higher pH of the lower gastrointestinal tract and are thus unavailable. Therefore, even basic drug moieties may result in having their availability characteristics improved as a result or protracting the residence in the gastric region.

The normal emptying time of the stomach is a problematical phenomena, varying widely, from a matter of a few minutes to as long as several hours, depending on many factors such as the time at which the last meal was administered, on the stress and anxiety of the individual, on the position and level of activity of the individual and other factors.

As a result of these physiological factors which influence gastric emptying time, absorption and the subsequent availability and reliability of drug response varies widely.

Drugs which are absorbed in the gastric region or upper portion of the small intestine, and which have either a low equilibrium solubility or a slow solubility rate, are poorly available on oral administration. The difficulty is that the drug tends to empty from the gastric region before it has had an opportunity to dissolve and be absorbed in a region of optimum availability. The availability of such drugs is highly variable and very sensitive to the aforementioned physiological factors. The oral route of administration is unreliable for such drugs. To date pharmaceutical manufacturers have had no choice but to live with poor availability or low reliability of absorption of such drugs on oral administration, since they have lacked an effective method of combatting the physiologic factors, notably gastric emptying, which make oral administration the variable route of drug dosing it is. Many common drugs fall in this category of low and variable oral availability such as the tetracycline antibiotics or the cephalosporin antibiotics and may other acidic and amphoteric drug agents. A dosage form which will provide a protracted gastric residence time would result in a system permitting improved oral administration of drugs.

Most prior art drug formulations which seek to release drugs for dissolution in the stomach or gastric region quickly release the drugs in an uncontrolled manner for immediate and uncontrolled availability. The result is blood levels and tissue concentration of the drug which peak to high levels at concentration well above that required to elicit the basic drug response, with the peak concentration of drug representing wasted drug or drug which may produce toxic effects. As the blood or tissue levels fall into a sub-therapeutic range, a second dose of administration is given with the result that subsequent peak concentrations tend to increase. On repetitive dosing, it is not uncommon to find peak levels which do build into a toxic region. The vast majority of both acidic and basic prior art drug formulations that at the present time provide immediate and rapid release may be classified as dump-type systems. In only a relatively few cases can a rapid drug release for dissolution and availability be justified. In all other cases, such rapid and immediate delivery of the drug by the drug product is both unnecessary and undesirable from the standpoint of theroretical design. It has, however, been necessary to design acidic drugs in dump systems to insure rapid dissolution of the acidic drug so that it is dissolved and available prior to or immediately after being emptied from the stomach. Such drug products tend to have a short duration of action and based on the high concentration of drug in the stomach may be irritating.

No effective prior art sustained action products of acidic drugs presently exists. Prior art sustained release mechanisms nearly always involve delaying the dissolution rate of the drug to produce the sustained response. As the dissolution rate of coated particles of drug or a coated tablet is delayed and prolonged, the dosage form will continue to move along the gastrointestinal tract into regions of increasingly poor absorption and availability. The only theoretically sound way to design a sustained release dosage form of an acidic drug is to maintain the drug in the gastric region where it has a high absorption efficiency; and at that site, to gradually meter the drug in solution to the system for absorption and effect. This the prior art has been unable to achieve.

No effective prior art technology has existed to provide controlled and prolonged drug release for drugs which are intended to act locally in the stomach, e.g., antacids, acidulants, enzymes, and the like. The duration of action of such locally acting materials has been uncontrolled and short. It has depended on such factors as: (1) dilution with the gastric contents, and (2) gastric emptying, which is highly variable and essentially uncontrolled physiological function.

Medicament formulations which overcome the prior art formulation deficiencies and have controlled gastric residence times of up to twelve hours are set forth in the copending application, Ser. No. 422,687, filed Dec. 7, 1973 by Gilbert S. Banker, entitled "Controlled Gastric Residence Time Medicament Formulations" and incorporated herein by reference thereto. However, it has been found that variable swellability is produced in the polymeric film coating of the medicament formulations of Ser. No. 422,687, due to the binding of the film coating to the medicament core, and depending upon the nature of the medicament core, this binding prevents, limits, and delays swelling of the coating.

The present invention, therefore, provides a method for promoting uniform rapid swelling of the dosage forms, as well as limiting the cross-linking of the polymer coating of the medicament formulations of Ser. No. 422,687, thereby providing constant permeability.

Broadly, this invention provides a method of preparing improved controlled gastric residence medicament formulations which comprises treating the polymeric film coating of such formulations with a volatile amine.

By volatile amine is meant those amines which are volatile at ambient temperature, and those amines which although not volatile at ambient temperature may be volatilized by raising the polymer treatment temperature and/or lowering the polymer treatment pressure (e.g., vacuum treatment) without causing a detrimental effect to the polymer being treated.

Among the volatile amines which may be utilized in the practice of this invention are anhydrous ammonia, methyl amine, ethyl amine, and the like.

The medicament formulations of this invention comprise tablets and/or capsules having permeable polymeric film surface systems capable of rapid hydration and swelling, e.g., with 5 to 10 minutes of contact with gastric fluid, to 200 to 1,000 percent or more of original formulation volume. The expanded permeable polymeric film permits free passage of water from the gastric fluid into the tablet or capsule, thus providing for controlled drug release under a positive osmotic pressure of the drug and/or other solute within the polymeric film membrane.

The polymeric systems which may be utilized in the practice of this invention are non-toxic or physiologically inert prepolymers and cross-linking agents capable of forming cross-linked systems which hydrate and swell or expand in gastric media. Included in the polymeric systems are the following:

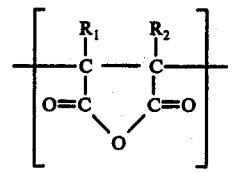

where $R_1$ and $R_2$ are independently, hydrogen, hydroxyl, halo having an atomic weight of 19 to 26 e.g., chloro or fluoro, alkyl having 1 to 16 carbon atoms, e.g., methyl, ethyl, propyl, isopropyl, pentyl, isopentyl, octyl, dodecyl, hexadecyl, substituted aralkyl or $SO_3H$, and the like; polymerized with alkyl vinyl ethers having 1 to 16 carbon atoms, preferably 1 to 4 carbon atoms, e.g., methyl vinyl ether, ethyl vinyl ether, n-propyl vinyl ether, isopropyl vinyl ether, n-butyl vinyl ether, isobutyl vinyl ether, amyl vinyl ether, hexyl vinyl ether, dodecyl vinyl ether, hexadecyl vinyl ether, and the like, aryl, e.g., phenyl tolyl, xylyl, napthyl, and the like, aralkyl, e.g., benzyl, and the like. Especially preferred as prepolymer (I) is unsubstituted maleic anhydride.

Comonomer components may also be copolymerized with the dicarboxylic acid anhydrides to form the prepolymer. Among the comonomers which may be utilized, are alkenes having 2 to 6 carbon atoms, such as ethylene, propylene, isopropylene, butadiene, and the like, styrene, or alkyl vinyl ethers wherein the alkyl moeity may contain from 1 to 12 carbon atoms such as methylvinylether, isopropylvinylether, and the like. The preferred comonomers are styrene, ethylene, or methylvinylether.

The ratio of anhydride monomer to the above described comonomers is from about 90:10 to 20:80 parts by weight of anhydride monomer to comonomer respectively, preferably 80:20 to 40:60 parts by weight of anhydride monomer to comonomer respectively.

| PREPOLYMER | CROSS-LINKING AGENT |
|---|---|
| Substituted or unsubstituted Dicarboxylic acid polymers, or Dicarboxylic acid anhydride polymers having 1 to 3 carbon atoms | Di or polyhydroxy compounds, diamines, polyfunctional amines, difunctional aromatic compounds, triols, aldopentoses, |
| Acrylic polymers Carboxy vinyl polymers Polyamines Polyhydroxyl polymers and Copolymers | hetopentoses, aldohexoses or polysacchorides |
| Amylose (from starch) Starch | Fatty acids Mixed anhydrides of acetic acid and citric acid, epichlorohydrin, or phosphorous oxychloride |

Representative of the substituted or unsubstituted dicarboxylic acid anhydrode prepolymers are polymers having the following as monomers: maleic anhydride, malonic anhydride, succinic anhydride, allyl succinic anhydride, phenyl maleic anhydride, mesaconic anhydride, phenylsuccinic anhydride, sulfomaleic anhydride, aconitic anhydride, benzylmalonic anhydride, itaconic anhydride, and the like.

Representative of the substituted or unsubstituted dicarboxylic acid prepolymers are polymers having the acid form of the above anhydride as a monomer.

The preferred prepolymers are polymers prepared from α,β-unsaturated dicarboxylic acid anhydrides of the following structural formula:

The molecular weight of the prepolymers utilized may vary from about 100,000 to 5,000,000 average molecular weight, preferably from about 250,000 to 2,000,000 average molecular weight.

Representative of the non-toxic cross-linking agents which may be utilized with the prepolymer systems are alkylene diols, such as 1,3-propylenediol, polyalkylene glycols, such as diethylene glycol or glycerine, polyethylene glycol, e.g., of molecular weight 400 to 2,000, polytetramethylglycol or methoxypolyethylene glycol, long chain dihydric compounds, such as polyoxyethylene sorbitan ethers, e.g., polyoxyethylene sorbitan monooleate or monolaurate, diamines, such as ethylenediamine, polyfunctional amines, such as triethylenetetramine or pentaethylene hexamine, and triols such as 1,2,3-butane triol.

It is also within the scope of this invention to include plasticizers, such as glycerol triacetate, ethylacetate, diethyl phthalate, dibutyl phthalate, di(n-butyl) sebecate, propylene glycol, polyethylene glycol, glycerin, sorbitol, and the like and mixtures thereof, such as glycerinpropylene glycol, sorbitol-glycerine, in the prepolymer systems. The plasticizer employed will depend on the prepolymer and cross-linking agent. However, for the preferred systems described above, glyceryl triacetate may be employed. The quantity of plasticizer will also vary, but the plasticizer may be present from about 8 parts by weight of prepolymer to 1 to 10, preferably 1 to 7, or preferably about 4 to 5 parts by weight of plasticizer.

While both the water soluble and water insoluble plasticizer disclosed above are useful in the prepolymer systems of this invention, the water soluble plasticizers offer certain advantages. Water soluble plasticizers provide a mechanism of attaining faster coat hydration, water penetration through the coating, coat swelling and drug release than the water insoluble plasticizers.

When a water soluble plasticizer is used in the polymer film formulations as the coating composition, it is possible that drug release may be too rapid. When such is the case, the water soluble plasticizer-polymer film may be overcoated with a polymer film containing a less polar plasticizer or a mixture of polar and non-polar plasticizers.

The drugs which may be utilized in the practice of this invention are preferably acid, basic or amphoteric drugs which are water soluble and are diffusable through the polymeric film membrane. Among the drugs which may utilized are those set forth in Ser. No. 422,687.

In the preparation of polymeric film coated tablets or capsules according to this invention, tablets or capsules are prepared using conventional tabletting or encapsulation techniques, and are then coated with a primary polymeric film. The coated dosage form is then exposed to amine vapor for from about 5 minutes to about 24 hours, preferably, 15 minutes to one hour. After the amine vapor exposure, an additional coating is applied to the dosage form and the formulation is cross-linked in a constant humidity atmosphere as will be described below. This cross-linking may be terminated at any desired point by exposing the second coating to amine vapors.

It is believed the volatile amine treatment of the first coat creates a barrier layer between the medicament core and the swellable outer polymeric film thus preventing any interaction between the swellable outer layer and the medicament core.

In a preferred embodiment of this invention the prepolymer (I) may be treated with volatile amine to convert the anhydride to the amide form and then to include the cross-linking agent and the plasticizer. The mixture is then applied as a primary film to the medicament core from a dilute coating solution. The secondary coating is then applied and cross-linked as described above.

In another preferred embodiment of this invention, the polymeric film is applied to the medicament core and cross-linked in a constant humidity chamber for a specific time period following which the dosage form is exposed to amine vapors for a period sufficient to cause all residual moieties to be converted to amides to eliminate any further cross-linking. As noted above, the degree of cross-linking of the polymeric coating whether a single coating or a combination of coatings may be terminated at any desired point by exposing the polymer coating to amine vapors. This amine treatment then effectively limits the permeability of the polymer coatings.

The total weight of the coatings on the core may vary widely depending on the release pattern and gastric residence time desired. However, the weight of the coatings on a tablet may be from about 25 to about 300 mg., preferably from about 40 to about 70 mg., and on a capsule from about 35 to about 500 mg., preferably about 50 to about 150 mg.

The polymeric films are prepared by dissolving prepolymer, e.g., ethylene maleic anhydride copolymer, cross-linking agent, e.g., poloxyethylene sorbitan monoleate and plasticizer, e.g., triacetin in a solvent, e.g., ethylacetate. Tablets or capsules are then coated using conventional techniques, e.g., immersion coating, with the above polymeric film solution. A preferred method of coating the dosage forms of this invention is using the coating apparatus described in U.S. Pat. No. 3,896,762. The second polymeric film on the coated tablets or capsules is then cross-linked by the application of heat in the presence of water, e.g., about 10° to 90° C., preferably 20° to 60° C., at 30 to 95 percent relative humidity, preferably 40 to 60 percent relative humidity for 4 to 200 hours, preferably 8 to 24 hours. cross-link the prepolymer on the tablets or capsules, within the tablet shipping container. For example, pharmaceutical tablets may be coated with polymeric film placed in a jar containing a predetermined amount of water and stored for a period of time at a predetermined temperature to promote cross-linking of the prepolymer.

In medicament formulations of this invention in which a drug having a high molecular weight, e.g., insulin or polypeptides is used, the drug may have a low diffusion rate through the polymeric membrane. In such instances, polymeric membrane opening materials may be used, which are soluble in gastric fluid. These materials are dispersed in the polymeric membrane and may include, for example, finely divided or micronized calcium carbonate. Upon contact with gastric fluid, the membrane opening materials dissolve in the gastric fluid leaving openings in the polymeric membrane through which the drug may pass.

It is also within the scope of this invention to coat the tablets or capsules with a binary polymeric film system. This binary system comprises an essentially water insoluble polymer component and a second polymer component which is hydratable in gastric fluid, and on partial hydration swells, or on complete hydration may dissolve. Upon exposure to gastric fluid the hydratable polymer of the binary film hydrates and swells to provide prolonged gastric residence, after which it may slowly dissolve and be preferentially leached-out from the coating, leaving with the passage of time a porous but intact network, which is increasingly composed of the insoluble polymer.

The advantage of the binary polymeric film is that its porosity increases with time, compensating for decreased drug concentration, within the membraneous fluid filled sac. In the non-binary polymer film coating of this invention, the film hydrates or swells to an equilibrium value corresponding to a maximum diffusional ability for the film. As drug diffuses from the polymer film, the concentration of drug within the sac decreases and the concentration gradient across the film membrane, which is the diffusional driving force, correspondingly decreases along with a decreased drug release rate. In this binary film system, the increasing porosity and diffusivity of the polymer film exactly or nearly compensates for the decreasing drug concentration gradient across the film with time, so that a constant release rate may be maintained, or the terminal release rate at the end of the diffusional process may actually increase.

Any water hydratable polymer described above may be combined with any compatible water insoluble polymer in the binary film system to produce controlled gastric residence, with constant or nearly constant drug release rate.

In the practice of this aspect of the invention, it has been found that the acids and anhydrides of the dicarboxylic acid prepolymers described above are compatible over a wide range of proportions with water insoluble carboxyl containing and carboxylate copolymers such as acrylates, e.g., methylmethacrylate, ethylmethacrylate, and the like. The hydratable, swellable polymer can be cross-linked or non-cross-linked. Should the swellable polymer be cross-linked, the cross-linking agents described above may be utilized.

In the binary polymeric film system, the ratio of insoluble polymer to hydratable, swellable polymer is from about 90:10 to 10:90, preferably 60:40 to 10:90.

The molecular weight range of the insoluble polymer may vary from about 25,000 to 3,000,000 average molecular weight, preferably 50,000 to 1,000,000 average molecular weight.

The commercial polymers, Gantrez AN(GAF Corp.) Poly(methylvinylether/maleic anhydride) (PVM/MA) have been found to give satisfactory results when used in the practice of this invention. They are a one to one molar ratio of vinylether to anhydride may be characterized as follows:

Gantrez AN-119 (PVM/MA-119) Av. molecular wt. 250,000; Specific Visosity 0.1–0.5;
Gantrez AN-139 (PVM/MA-139) Av. molecular wt. 500,000; Specific Viscosity 1.0–1.4;
Gantrez AN-149 (PVM/MA-149) Av. molecular wt. 750,000; Specific Viscosity 1.4–2.0;
Gantrez AN-169 (PVM/MA-169) Av. molecular wt. 1,250,000; Specific Viscosity 2.6–3.5; and
Gantrez AN-179 (PVM/MA-179) Av. molecular wt. 1,500,000

The controlled gastric residence dosage form of this invention is based on a film membrane applied to a solid dosage form. The membrane is permeable to water and gastric fluid permitting fluid to enter the coated dosage form, dissolve drug which may be present, and provide for controlled drug release by a diffusional process through the film-membrane system. In other instances, diffusional rates of gastric acid into the membrane sac where neutralization occurs may be related to antacid activity. Rate and extent of membrane swelling on film hydration in the gastric environment will also effect the overall diffusional process and drug release.

In other applications of the invention, particularly where insoluble or only sparingly or slightly soluble drugs are involved, the controlled gastric residence coating may be applied as a binary film system in which a hydratable and soluble polymer provides for film opening. Alternatively a dispersed finely divided solid, soluble in gastric media provides for film opening. Also within the scope of this invention, one-half or part of the dosage form, layer tablets, compression coated tablets, and/or capsules may be coated with a polymeric film, which film serves as an anchor to hold the dosage form in the stomach. In such an instance none of the drug, part of the drug or a second drug may be released through the film membrane, while an insoluble drug may be released from the uncoated portion immediately, after a delayed period, or continuously, depending on the design of the dosage form and the release profile sought.

In coating the above anchor concept wherein about half of the dosage form is coated, the coating apparatus of U.S. Pat. No. 3,896,762, noted above is particularly advantageous. Utilizing this coating apparatus achieves economics of operation in simplifying the handling of the dosage form and in a substantial increase in production rate.

An additional feature of this invention is to perforate the dosage form film coat with one or more microholes to form an opening or valve for drug release upon the swelling or expansion of the film coating. The microholes may be from about 0.25 to 3 mm., preferably 1 to 1.5 mm. This microhole technique is particularly advantageous when insoluble drugs, such as antiacids are within the medicament core.

While tablets and/or capsules are the preferred film coated dosage forms of this invention, it is also within the scope of this invention to coat microcapsules. These capsules may be coated using the conventional technique of air suspension or the techniques described above.

The following illustrative but non-limiting examples describe some of the flexibility and application range of this invention.

EXAMPLE

No. 0 capsules containing:
1. 500 mg. potassium chloride USP
   15 mg. talc
   260 mg. Sucrose USP
2. 275.4 mg. tetracycline hydrochloride
   4.0 mg. talc
   400.0 mg. Sucrose USP
were coated with:
PVM/MA 169-Tween 20Triacetin[1] polymer films having the following ratios:
[1]Polymer-PVM/MA 169-poly(methylvinylether)maleic anhydride cross-linking agent-Tween 20-polyoxyethylene sorbitan monolaurate plasticizer-triacetin

| PVM/MA 169 | Tween 20 | Triacetin |
|---|---|---|
| 8 | 0.1 | 2 |
| 8 | 0.1 | 4 |
| 8 | 0.1 | 6 |
| 8 | 0.1 | 8 |
| 8 | 0.28 | 2 |
| 8 | 0.28 | 4 |
| 8 | 0.28 | 6 |
| 8 | 0.28 | 8 |
| 8 | 0.56 | 2 |
| 8 | 0.56 | 4 |
| 8 | 0.56 | 6 |
| 8 | 0.56 | 8 |
| 8 | 0.76 | 2 |
| 8 | 0.76 | 4 |
| 8 | 0.76 | 6 |
| 8 | 0.76 | 8 |
| 8 | 1.12 | 2 |
| 8 | 1.12 | 4 |
| 8 | 1.12 | 6 |
| 8 | 1.12 | 8 |
| 8 | 2.0 | 2 |
| 8 | 2.0 | 4 |

| PVM/MA 169 | Tween 20 | Triacetin |
|---|---|---|
| 8 | 2.0 | 6 |
| 8 | 2.0 | 8 |

The capsules having the compositions of (1) and (2) above were coated by dipping them in solutions having the above PVM/MA-Tween 20-Triacetin ratios in 100 ml. of 25 percent acetone and 75 percent ethylacetate v/v.

A first coat of 10 mg. was applied to each capsule followed by treatment with anhydrous ammonia. Capsules having the above film compositions were ammonia treated for time periods of 5 minutes, 15 minutes, 30 minutes, 1 hour, 2 hours, 4 hours, 8 hours, 16 hours, and 24 hours.

Following the ammonia treatment, he capsules were then coated to a total coat weight of 100 mg. and then cross-linked at ambient temperature at 85 percent relative humidity for 4 days.

No failures in swellability of the film coating were noted for the ammonia treated capsules. Capsules prepared as above but without the ammonia treatment swelled erratically.

What is claimed is:

1. A method of preparing a controlled gastric residence medicament formulation comprising:
    a. applying a first coating to a medicament core of a non-toxic, water hydratable and water permeable, polymeric film comprising a ratio of eight parts of a prepolymer of the formula:

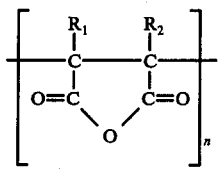

wherein
$R_1$ and $R_2$ are independently, hydrogen, hydroxy, halo having an atomic weight of 19 to 36, alkyl having 1 to 16 carbon atoms, substituted aralkyl or $SO_3H$; polymerized with alkylvinylether having 1 to 16 carbon atoms, alkene, aryl, aralkyl, or substituted aralkyl and represents an average polymer molecular weight of from 100,000 to 5,000,000; said prepolymer cross-linked with from about 0.15 to about 2 parts of a cross-linking agent selected from the group consisting of alkylene diol, polyalkylene glycols, polyoxyethylene sorbitan ethers, diamines, and triols, about 1 to about 10 parts of plasticizer selected from the group consisting of glycerol triacetate, ethylacetate, diethylphthalate, dibutyl phthalate, di(n-butyl)sebacate, propylene glycol, polyethylene glycol, glycerin, sorbitol and mixtures thereof;

b. treating the polymeric film coated core with a volatile amine vapor for about 5 minutes to about 24 hours;

c. coating the amine treated polymeric film core with a second coating of the polymeric film of step (a); and d. maintaining the coated medicament formulation at a relative humidity of from about 30 to about 95 percent at a temperature of from about 10° to about 90° C. for about 4 to 200 hours to crosslink said second coating.

2. The method according to claim 1, wherein the volatile amine is selected from the group consisting of anhydrous ammonia, methyl amine, or ethyl amine.

3. The method according to claim 2, wherein the volatile amine is anhydrous ammonia.

4. The method according to claim 1, wherein said cross-linking agent is from about 0.15 to 1.0 parts and said plasticizer is from about 4 to 5 parts.

5. The method according to claim 4, wherein said formulation is cross-linked at from about 20° C. to 60° C. at from about 40 to 60 percent relative humidity for about 24 to 120 hours.

6. The method according to claim 5, wherein $R_1$ and $R_2$ are hydrogen and the prepolymer is polymerized with methylvinylether.

7. The method according to claim 6, wherein the ammonia treatment is from about 15 minutes to about 1 hour.

8. A method of preparing a controlled gastric residence medicament formulation comprising:
    a. applying a first coating to a medicament core of a non-toxic, water hydratable and water permeable, copolymer film, said copolymeric film comprising a ratio of eight parts of a first prepolymer of the formula:

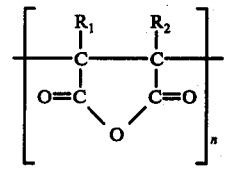

(wherein
$R_1$, $R_2$, and $n$ are as defined in claim 1 and a second prepolymer selected from the group consisting of alkenes having 2 to 6 carbon atoms, alkylvinylether, wherein the alkyl radical has from 1 to 12 carbon atoms and styrene; said first prepolymer cross-linked with from about 0.15 to 2 parts of a cross-linking agent selected from the group consisting of alkylene diol, polyalkylene glycols, polyoxyethylene sorbitan ethers, diamines, and triols, about 1 to 10 parts of plasticizer selected from the group consisting of glycerol triacetate, ethylacetate, diethyl phthalate, dibutyl phthalate, di(n-butyl) sebecate, propylene glycol, polyethylene glycol, glycerin, sorbitol, and mixtures thereof;)

b. treating the copolymeric film coated core with a volatile amine vapor for about 5 minutes to about 24 hours;

c. coating the amine treated copolymeric film core with a second coating of polymeric film of step (a); and d. maintaining the coated medicament formulation at a relative humidity of 30 to 95 percent at a temperature of 10° to 90° C., for 4 to 200 hours to crosslink said second coating.

* * * * *